(12) United States Patent
Van Buel et al.

(10) Patent No.: US 10,331,043 B2
(45) Date of Patent: Jun. 25, 2019

(54) OPTIMIZATION OF TARGET ARRANGEMENT AND ASSOCIATED TARGET

(71) Applicant: ASML Netherlands B.V., Veldhoven (NL)

(72) Inventors: Henricus Wilhelmus Maria Van Buel, 's-Hertogenbosch (NL); Johannes Marcus Maria Beltman, Knegsel (NL); Xing Lan Liu, Veldhoven (NL); Hendrik Jan Hidde Smilde, Veldhoven (NL); Richard Johannes Franciscus Van Haren, Waalre (NL)

(73) Assignee: ASML Netherlands B.V., Veldhoven (NL)

( * ) Notice: Subject to any disclaimer, the term of this patent is extended or adjusted under 35 U.S.C. 154(b) by 147 days.

(21) Appl. No.: 15/118,440

(22) PCT Filed: Jan. 29, 2015

(86) PCT No.: PCT/EP2015/051796
§ 371 (c)(1),
(2) Date: Aug. 11, 2016

(87) PCT Pub. No.: WO2015/124397
PCT Pub. Date: Aug. 27, 2015

(65) Prior Publication Data
US 2017/0176871 A1     Jun. 22, 2017

(30) Foreign Application Priority Data
Feb. 21, 2014   (EP) .................................... 14156125

(51) Int. Cl.
*G03F 7/20* (2006.01)
*G01N 21/93* (2006.01)
*G01N 21/956* (2006.01)

(52) U.S. Cl.
CPC ......... *G03F 7/70683* (2013.01); *G01N 21/93* (2013.01); *G01N 21/956* (2013.01); *G03F 7/70633* (2013.01)

(58) Field of Classification Search
CPC .. G01N 21/93; G01N 21/956; G03F 7/70616; G03F 7/70625; G03F 7/70633;
(Continued)

(56) References Cited

U.S. PATENT DOCUMENTS 7,791,727 B2   9/2010   Den Boef et al.
7,873,504 B1   1/2011   Bevis
(Continued)

FOREIGN PATENT DOCUMENTS

CN   1996151        7/2007
JP   2005-337919   12/2005
(Continued)

OTHER PUBLICATIONS

Chinese Office Action dated May 12, 2017 in corresponding Chinese Patent Application No. 201580009522.0 (19 pages).
(Continued)

*Primary Examiner* — Gordon J Stock, Jr.
(74) *Attorney, Agent, or Firm* — Pillsbury Winthrop Shaw Pittman LLP

(57) ABSTRACT

A method of devising a target arrangement, and associated target and reticle. The target includes a plurality of gratings, each grating having a plurality of substructures. The method includes: defining a target area; locating the substructures within the target area so as to form the gratings; and locating assist features at the periphery of the gratings, the assist features being configured to reduce measured intensity peaks at the periphery of the gratings. The method may include an optimization process including modelling a resultant image obtained by inspection of the target using a
(Continued)

metrology process; and evaluating whether the target arrangement is optimized for detection using a metrology process.

20 Claims, 8 Drawing Sheets

(58) Field of Classification Search
CPC . G03F 7/70641; G03F 7/70683; G01B 11/02; G01B 11/022; G01B 11/024; G01B 11/14
See application file for complete search history.

(56) References Cited

U.S. PATENT DOCUMENTS

| | | | |
|---|---|---|---|
| 8,411,287 B2 | 4/2013 | Smilde et al. | |
| 8,705,007 B2 | 4/2014 | Cramer et al. | |
| 9,069,264 B2 | 6/2015 | Warnaar et al. | |
| 9,081,303 B2 | 7/2015 | Cramer et al. | |
| 9,134,256 B2 | 9/2015 | Smilde et al. | |
| 9,140,998 B2 | 9/2015 | Smilde et al. | |
| 9,261,772 B2 | 2/2016 | Quintanilha | |
| 2006/0033921 A1 | 2/2006 | Den Boef et al. | |
| 2006/0117293 A1* | 6/2006 | Smith | G03F 7/70633 716/50 |
| 2009/0116014 A1* | 5/2009 | Smith | G03F 7/705 356/401 |
| 2010/0175033 A1 | 7/2010 | Adel et al. | |
| 2010/0201963 A1 | 8/2010 | Cramer et al. | |
| 2011/0027704 A1 | 2/2011 | Cramer et al. | |
| 2011/0043791 A1 | 2/2011 | Smilde et al. | |
| 2012/0044470 A1 | 2/2012 | Smilde et al. | |
| 2012/0123581 A1 | 5/2012 | Smilde et al. | |
| 2012/0156881 A1* | 6/2012 | Haffner | H01L 21/0337 438/703 |
| 2013/0050501 A1 | 2/2013 | Warnaar et al. | |
| 2013/0258310 A1 | 10/2013 | Smilde et al. | |
| 2013/0271740 A1 | 10/2013 | Quintanilha | |
| 2014/0065736 A1* | 3/2014 | Amir | H01L 23/544 438/14 |
| 2015/0050755 A1* | 2/2015 | Ausschnitt | H01L 22/12 438/14 |
| 2015/0138523 A1 | 5/2015 | Jak et al. | |
| 2015/0355554 A1 | 12/2015 | Mathijssen | |
| 2016/0061589 A1* | 3/2016 | Bhattacharyya | G01B 11/14 356/620 |

FOREIGN PATENT DOCUMENTS

| | | |
|---|---|---|
| JP | 2009-532862 | 9/2009 |
| JP | 2012-080131 | 4/2012 |
| TW | 201400993 | 1/2014 |
| WO | 2009/078708 | 6/2009 |
| WO | 2009/106279 | 9/2009 |
| WO | 2013/026598 | 2/2013 |
| WO | 2013/143814 | 10/2013 |
| WO | 2013/178422 | 12/2013 |
| WO | 2014/138057 | 9/2014 |

OTHER PUBLICATIONS

Japanese Office Action dated Sep. 7, 2017 in corresponding Japanese Patent Application No. 2016-550741.
International Search Report and Written Opinion dated May 28, 2015 in corresponding International Patent Application No. PCT/EP2015/051796.
Taiwan Office Action dated Aug. 29, 2016 in corresponding Taiwan Patent Application No. 104105139.
Taiwan Office Action dated Dec. 20, 2016 in corresponding Taiwan Patent Application No. 104105139.
Korean Office Action dated Jan. 17, 2018 in corresponding Korean Patent Application No. 10-2016-7025790.
Chinese Office Action dated Jan. 19, 2018 in corresponding Chinese Patent Application No. 201580009522.0.
Japanese Office Action dated Mar. 6, 2018 in corresponding Japanese Patent Application No. 2016-550741.

* cited by examiner

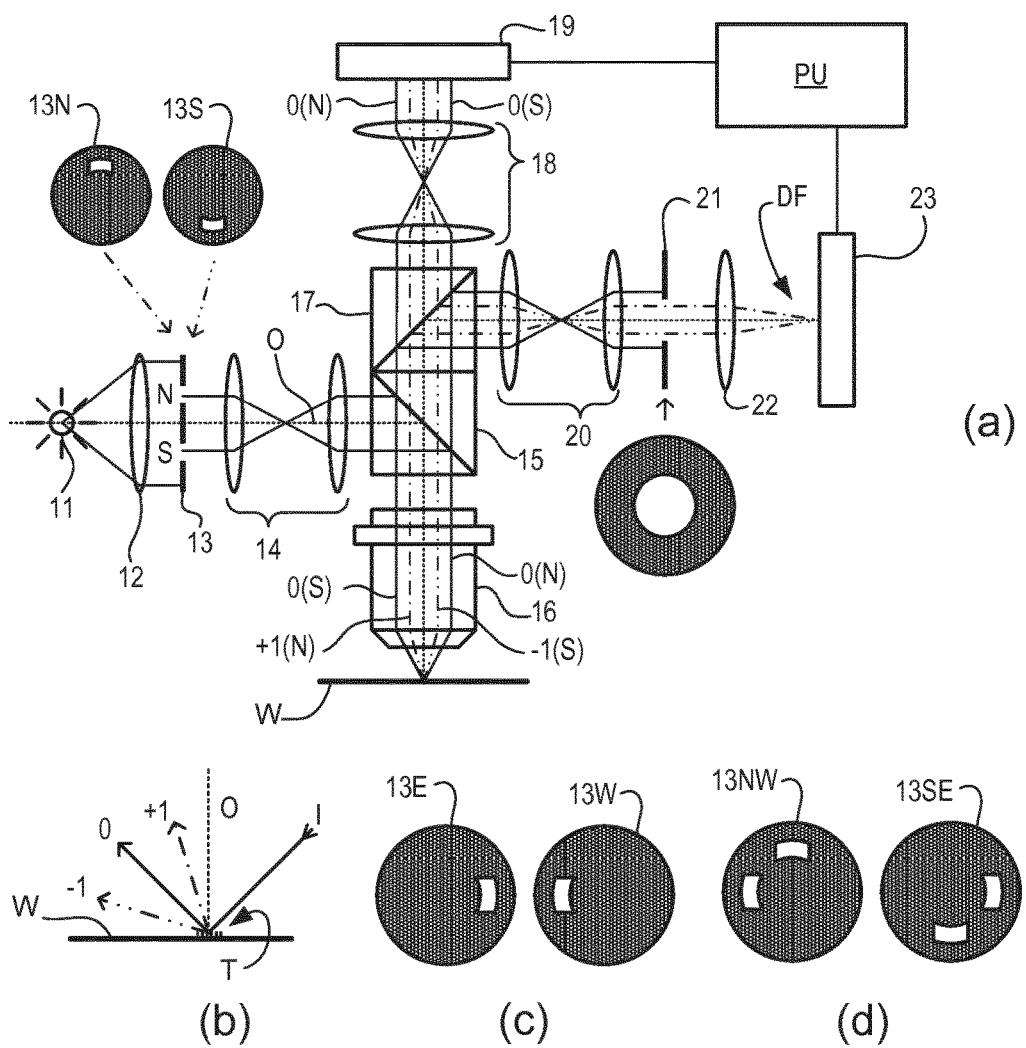
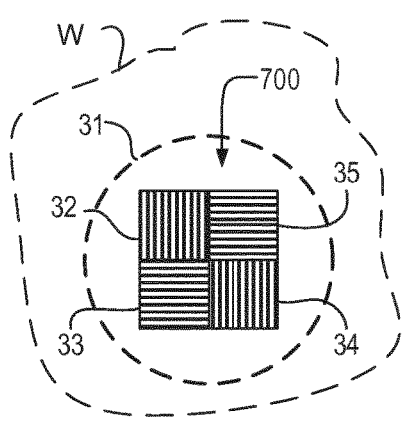
Fig. 4 (PRIOR ART)
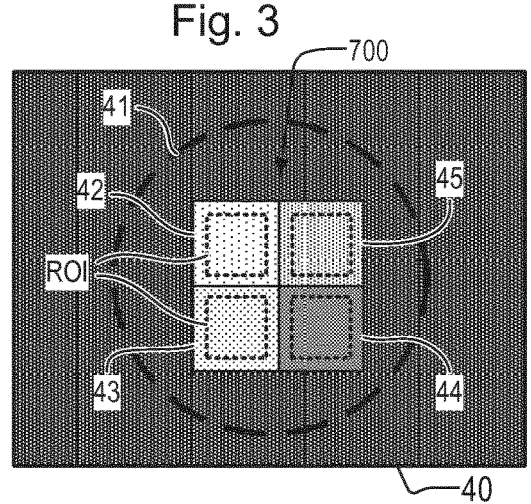
Fig. 5 (PRIOR ART)

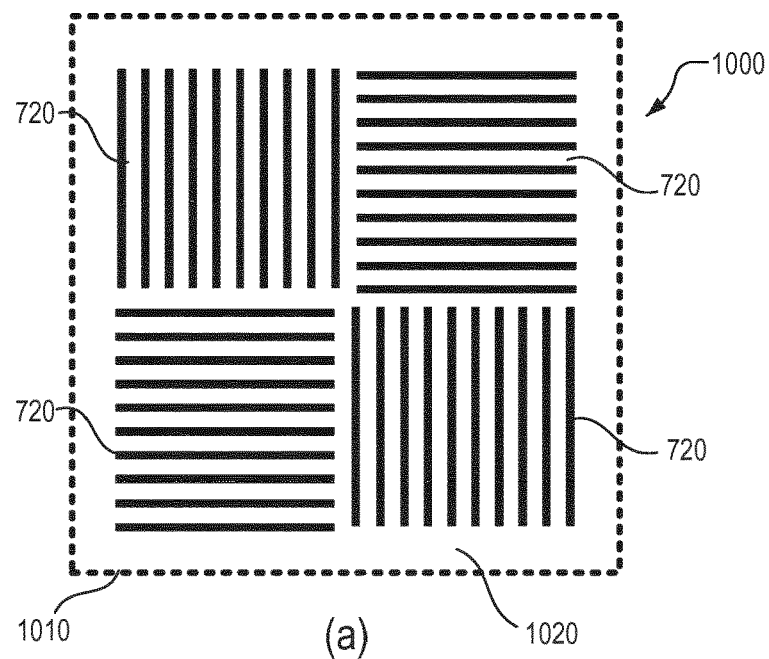
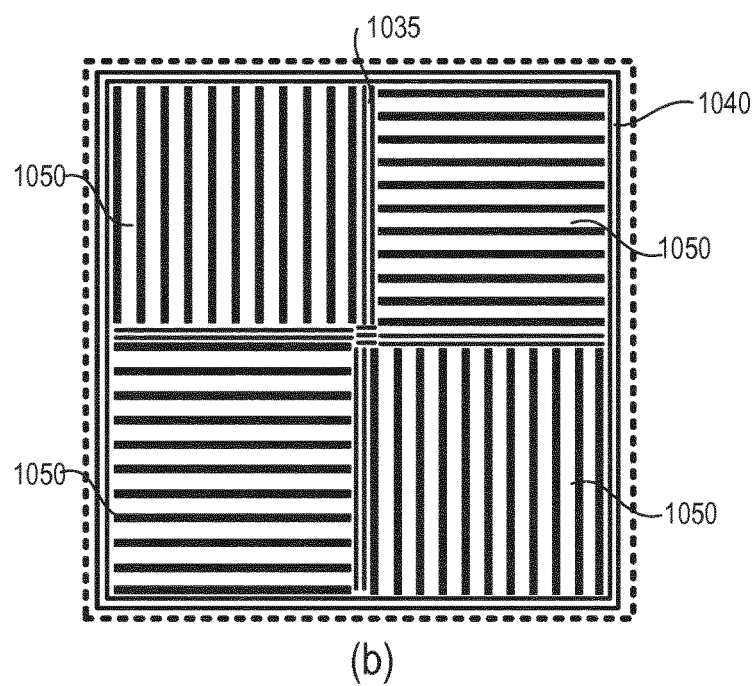
Fig. 10

OPTIMIZATION OF TARGET ARRANGEMENT AND ASSOCIATED TARGET

CROSS-REFERENCE TO RELATED APPLICATIONS

This application is the U.S. national phase entry of PCT patent application no. PCT/EP2015/051796, which was filed on Jan. 29, 2015, which claims the benefit of priority of EP patent application no. 14156125, which was filed on Feb. 21, 2014, and which is incorporated herein in its entirety by reference.

BACKGROUND

Field of the Invention

The present invention relates to methods and apparatus for semiconductor wafer metrology, for example, in the manufacture of devices by lithographic techniques. More specifically, it relates to optimization procedures for arrangement of a target, and of a target so arranged.

Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti parallel to this direction. It is also possible to transfer the pattern from the patterning device to the substrate by imprinting the pattern onto the substrate.

In order to monitor the lithographic process, parameters of the patterned substrate are measured. Parameters may include, for example, the overlay error between successive layers formed in or on the patterned substrate and critical linewidth of developed photosensitive resist. This measurement may be performed on a product substrate and/or on a dedicated metrology target. Metrology targets (or marks) may comprise, for example, combinations of horizontal and vertical bars, forming for example periodic structures such as gratings.

There are various techniques for making measurements of the microscopic structures formed in lithographic processes, including the use of scanning electron microscopes and various specialized tools. A fast and non-invasive form of specialized inspection tool is a scatterometer in which a beam of radiation is directed onto a target on the surface of the substrate and properties of the scattered or reflected beam are measured.

Various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target structure by iterative approaches such as rigorous coupled wave analysis or finite element methods; library searches; and principal component analysis.

Examples of known scatterometers include angle-resolved scatterometers of the type described in US2006033921A1 and US2010201963A1. The targets used by such scatterometers are relatively large, e.g., 40 µm by 40 µm, gratings and the measurement beam generates a spot that is smaller than the grating (i.e., the grating is underfilled). This simplifies mathematical reconstruction of the target as it can be regarded as infinite.

To limit the real-estate consumption for metrology purposes on each production wafer, metrology and alignment targets are being reduced in size. For example, target-sizes for overlay metrology range between 20×20 µm$^2$ to 10×10 µm$^2$. The use of smaller target-sizes is under study. Typically such targets are measured using "dark field" scatterometry in which the zeroth order of diffraction (corresponding to a specular reflection) is blocked, and only one or more higher orders are processed to create a gray scale image of the target (i.e. 'dark field' image). Diffraction-based overlay using this dark field technique enables overlay measurements on smaller targets, and is known as micro-diffraction based overlay (µDBO). Examples of dark field metrology can be found in international patent applications WO2009/078708, WO2009/106279, WO2013178422 and WO2013/143814. Further developments of the technique have been described in published patent publications US20110027704A, US20110043791A, US20120044470A US20120123581A, US20130258310A and US20130271740A; and in the U.S. patent applications 61/652,552 and 61/803,673. These targets can be smaller than the illumination spot and may be surrounded by product structures on a wafer. Thus, 'composite' targets (e.g. target comprising a plurality of individual grating portions of different overlay biases) can be entirely measured in one image. Therefore, the grating edges are also visible in the gray scale images of the target. The grating edges often present intensity levels that deviate from the average grating intensity (referred to herein as 'edge effects').

After image post processing (e.g. pattern recognition), regions-of-interest (ROIs) within each individual grating may be identified in the dark field image. An average grating intensity can be calculated for each ROI, while excluding the influence of the edge effects. Asymmetry of the grating structure, and hence overlay error, can then be inferred from average intensities.

As such, the average grating intensity is inferred from, for instance, a few CCD image sensor pixels (i.e. size of the selected ROIs on the sensor), corresponding to the center of the grating in the dark field image.

A current µDBO target design/layout is based on infinitely large gratings. Gratings features such as the line space dimensions, pitch, sub-segmentation etc., are optimized, depending on the application. The gratings are positioned around predefined grating centers in a region defining the target.

Computational lithography modeling (e.g. Litho-OPC, where OPC stands for optical proximity correction) is commonly used to design and optimize printable targets. The target layout may include sub-resolution 'assist features' (i.e. not detected by the sensor) to improve the dark field image resolution. These assist features may be located at arbitrary positions around 'detectable' target structures (e.g. around one of the target gratings and/or around wafer locations allocated to contain targets, also called target region) and can be used by the pattern recognition process. By generating 'empty' regions around the 'detectable' target structures, the pattern recognition process can then identify the position of the ROI with substantially greater accuracy than using only, for example, the edges of the grating. By providing recognizable assist features which are two, three or more times as numerous as for instance the boundaries of the target gratings, the accuracy of recognizing the ROI can be increased. However, the nominal region defining the target is consequently enlarged, for example, from 10×10 $\mu m^2$ to 12×12 $\mu m^2$ for $\mu$DBO targets.

It is desirable to provide an improved target design methodology and consequently improved targets.

SUMMARY OF THE INVENTION

In a first aspect of the invention there is provided a method of devising a target arrangement, said target comprising a plurality of gratings, each grating comprising a plurality of substructures, said method comprising the steps of: defining a target area; locating said substructures within the target area so as to form said gratings; and locating assist features at the periphery of said gratings, said assist features being configured to reduce measured intensity peaks at the periphery of said gratings.

In a second aspect of the invention there is provided a target comprising: a plurality of gratings, each grating comprising a plurality of substructures; assist features comprising lines having a pitch substantially smaller than the pitch of said gratings; wherein said target comprises assist features at the periphery of said gratings, said assist features being configured to reduce measured intensity peaks at the periphery of said gratings. Also disclosed is a method of devising a target arrangement, said target comprising a plurality of gratings, each grating comprising a plurality of substructures, said method comprising the steps of: defining a target area; locating said substructures within the target area so as to form said gratings; modelling a resultant image obtained by inspection of the target using a metrology process; and evaluating whether said target arrangement is optimized for detection using a metrology process.

BRIEF DESCRIPTION OF THE DRAWINGS

Embodiments of the invention will now be described, by way of example only, with reference to the accompanying drawings in which:

FIG. 3(a) is a schematic diagram of a dark field scatterometer for use in measuring targets according to embodiments of the invention using a first pair of illumination apertures, FIG. 3(b) is a detail of diffraction spectrum of a target grating for a given direction of illumination, FIG. 3(c) is a schematic diagram of a second pair of illumination apertures providing further illumination modes in using the scatterometer for diffraction based overlay measurements and FIG. 3(d) is a schematic diagram of a third pair of illumination apertures combining the first and second pair of apertures;

FIG. 4 depicts a known form of multiple grating metrology target and an outline of a measurement spot on a substrate;

FIG. 5 depicts an image of the target of FIG. 4 obtained in the scatterometer of FIG. 3;

FIG. 8(b), FIG. 8(c), FIG. 8(d), FIG. 8(e) and FIG. 8(f) illustrate an example of a non-optimized target layout and, and a target layout according to an embodiment of the invention and of resulting dark field images of these targets inspected using different wavelengths;

FIG. 10 (a) and FIG. 10(b) illustrate an example of a non-optimized target layout and, and a target layout according to an embodiment of the invention and resulting dark field images of these targets inspected using different wavelengths;

DETAILED DESCRIPTION OF EXEMPLARY EMBODIMENTS

Before describing embodiments of the invention in detail, it is instructive to present an example environment in which embodiments of the present invention may be implemented.

Figures 1, 2:
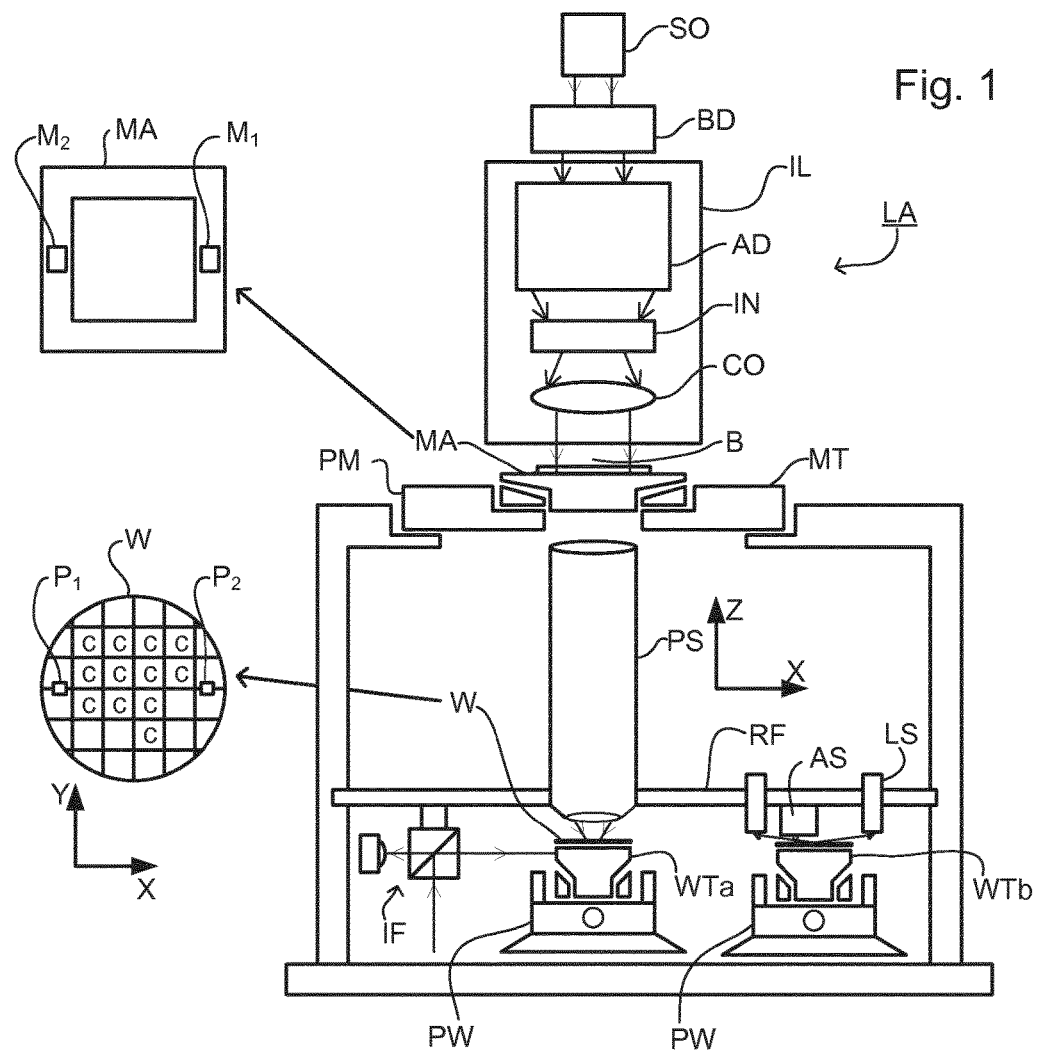
FIG. 1 depicts a lithographic apparatus according to an embodiment of the invention.
FIG. 2 depicts a lithographic cell or cluster according to an embodiment of the invention.

FIG. 1 schematically depicts a lithographic apparatus LA. The apparatus includes an illumination system (illuminator) IL configured to condition a radiation beam B (e.g., UV radiation or DUV radiation), a patterning device support or support structure (e.g., a mask table) MT constructed to support a patterning device (e.g., a mask) MA and connected to a first positioner PM configured to accurately position the patterning device in accordance with certain parameters; a substrate table (e.g., a wafer table) WT constructed to hold a substrate (e.g., a resist coated wafer) W and connected to a second positioner PW configured to accurately position the substrate in accordance with certain parameters; and a projection system (e.g., a refractive projection lens system) PS configured to project a pattern imparted to the radiation beam B by patterning device MA onto a target portion C (e.g., including one or more dies) of the substrate W.

The illumination system may include various types of optical components, such as refractive, reflective, magnetic, electromagnetic, electrostatic or other types of optical components, or any combination thereof, for directing, shaping, or controlling radiation.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support may be a frame or a table, for example, which may be fixed or movable as required. The patterning device support may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross section.

The radiation beam B is incident on the patterning device (e.g., mask) MA, which is held on the patterning device support (e.g., mask table MT), and is patterned by the patterning device. Having traversed the patterning device (e.g., mask) MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan. In general, movement of the patterning device support (e.g., mask table) MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the patterning device support (e.g., mask table) MT may be connected to a short-stroke actuator only, or may be fixed.

Patterning device (e.g., mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies. Small alignment markers may also be included within dies, in amongst the device features, in which case it is desirable that the markers be as small as possible and not require any different imaging or process conditions than adjacent features.

The depicted apparatus could be used in a variety of modes. In a scan mode, the patterning device support (e.g., mask table) MT and the substrate table WT are scanned synchronously while a pattern imparted to the radiation beam is projected onto a target portion C (i.e., a single dynamic exposure). The velocity and direction of the substrate table WT relative to the patterning device support (e.g., mask table) MT may be determined by the (de-)

magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion. Other types of lithographic apparatus and modes of operation are possible, as is well-known in the art. For example, a step mode is known. In so-called "maskless" lithography, a programmable patterning device is held stationary but with a changing pattern, and the substrate table WT is moved or scanned.

Combinations and/or variations on the above described modes of use or entirely different modes of use may also be employed.

Lithographic apparatus LA is of a so-called dual stage type which has two substrate tables WTa, WTb and two stations—an exposure station and a measurement station—between which the substrate tables can be exchanged. While one substrate on one substrate table is being exposed at the exposure station, another substrate can be loaded onto the other substrate table at the measurement station and various preparatory steps carried out. The preparatory steps may include mapping the surface control of the substrate using a level sensor LS and measuring the position of alignment markers on the substrate using an alignment sensor AS.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

A metrology apparatus (scatterometer) is shown in FIG. 3(a). A grating target T and diffracted rays are illustrated in more detail in FIG. 3(b). More detail of the apparatus and variations in its forma and usage are provided in US 2011027704 and other prior patent applications, mentioned above. The entire contents of those prior applications are incorporated herein by reference. The scatterometer may be a stand-alone device or incorporated in either the lithographic apparatus LA, e.g., at the measurement station, or the lithographic cell LC. An optical axis, which has several branches throughout the apparatus, is represented by a dotted line O. In this apparatus, light emitted by source 11 (e.g., a xenon lamp) is directed onto substrate W via a beam splitter 15 by an optical system comprising lenses 12, 14 and objective lens 16. These lenses are arranged in a double sequence of a 4F arrangement. A different lens arrangement can be used, provided that it still provides a substrate image onto a detector, and simultaneously allows for access of an intermediate pupil-plane for spatial-frequency filtering. Therefore, the angular range at which the radiation is incident on the substrate can be selected by defining a spatial intensity distribution in a plane that presents the spatial spectrum of the substrate plane, here referred to as a (conjugate) pupil plane. In particular, this can be done by inserting an aperture plate 13 of suitable form between lenses 12 and 14, in a plane which is a back-projected image of the objective lens pupil plane. In the example illustrated, aperture plate 13 has different forms, labeled 13N and 13S, allowing different illumination modes to be selected. The aperture plates in the present examples form various off-axis illumination modes. In the first illumination mode, aperture plate 13N provides off-axis illumination from a direction designated, for the sake of description only, as 'north'. In a second illumination mode, aperture plate 13S is used to provide similar illumination, but from an opposite direction, labeled 'south'. Other modes of illumination are possible by using different apertures. The rest of the pupil plane is desirably dark as any unnecessary light outside the desired illumination mode will interfere with the desired measurement signals.

As shown in FIG. 3(b), grating target T is placed with substrate W normal to the optical axis O of objective lens 16. A ray of illumination I impinging on target T from an angle off the axis O gives rise to a zeroth order ray (solid line O) and two first order rays (dot-chain line +1 and double dot-chain line −1). It should be remembered that with an overfilled small target grating, these rays are just one of many parallel rays covering the area of the substrate including metrology target T and other features. Where a composite grating target is provided, each individual grating within the target will give rise to its own diffraction spectrum. Since the aperture in plate 13 has a finite width (necessary to admit a useful quantity of light), the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown. Note that the grating pitches and illumination angles can be designed or adjusted so that the first order rays entering the objective lens are closely aligned with the central optical axis. The rays illustrated in FIGS. 3(a) and 3(b) are shown somewhat off axis, purely to enable them to be more easily distinguished in the diagram.

At least the 0 and +1 orders diffracted by the target on substrate W are collected by objective lens 16 and directed back through beam splitter 15. Returning to FIG. 3(a), both the first and second illumination modes are illustrated, by designating diametrically opposite apertures labeled as north (N) and south (S). When the incident ray I is from the north side of the optical axis, that is when the first illumination mode is applied using aperture plate 13N, the +1 diffracted rays, which are labeled +1(N), enter the objective lens 16. In contrast, when the second illumination mode is applied using aperture plate 13S the −1 diffracted rays (labeled −1(S)) are the ones which enter the lens 16.

A second beam splitter 17 divides the diffracted beams into two measurement branches. In a first measurement branch, optical system 18 forms a diffraction spectrum (pupil plane image) of the target on first sensor 19 (e.g. a CCD or CMOS sensor) using the zeroth and first order diffractive beams. Each diffraction order hits a different point on the sensor, so that image processing can compare and contrast orders. The pupil plane image captured by sensor 19 can be used for focusing the metrology apparatus and/or normalizing intensity measurements of the first order beam. The pupil plane image can also be used for asymmetry measurement as well as for many measurement purposes such as reconstruction, which are not the subject of the present disclosure. The first examples to be described will use the second measurement branch to measure asymmetry.

In the second measurement branch, optical system 20, 22 forms an image of the target on the substrate W on sensor 23

(e.g. a CCD or CMOS sensor). In the second measurement branch, an aperture stop 21 is provided in a plane that is conjugate to the pupil-plane. Aperture stop 21 functions to block the zeroth order diffracted beam so that the image of the target formed on sensor 23 is formed only from the −1 or +1 first order beam. The images captured by sensors 19 and 23 are output to image processor and controller PU, the function of which will depend on the particular type of measurements being performed. Note that the term 'image' is used here in a broad sense. An image of the grating lines as such will not be formed on sensor 23, if only one of the −1 and +1 orders is present.

The particular forms of aperture plate 13 and field stop 21 shown in FIG. 3 are purely examples. In another embodiment of the invention, on-axis illumination of the targets is used, and an aperture stop with an off-axis aperture is used to pass substantially only one first order of diffracted light to the sensor. (The apertures shown at 13 and 21 are effectively swapped in that case.) In yet other embodiments, 2nd, 3rd and higher order beams (not shown in FIG. 3) can be used in measurements, instead of or in addition to the first order beams.

In order to make the illumination adaptable to these different types of measurement, the aperture plate 13 may comprise a number of aperture patterns formed around a disc, which rotates to bring a desired pattern into place. Alternatively or in addition, a set of plates 13 could be provided and swapped, to achieve the same effect. A programmable illumination device such as a deformable mirror array or transmissive spatial light modulator can be used also. Moving mirrors or prisms can be used as another way to adjust the illumination mode.

As just explained in relation to aperture plate 13, the selection of diffraction orders for imaging can alternatively be achieved by altering the pupil-stop 21, or by substituting a pupil-stop having a different pattern, or by replacing the fixed field stop with a programmable spatial light modulator. In that case the illumination side of the measurement optical system can remain constant, while it is the imaging side that has first and second modes. In practice, there are many possible types of measurement method, each with its own advantages and disadvantages. In one method, the illumination mode is changed to measure the different orders. In another method, the imaging mode is changed. In a third method, the illumination and imaging modes remain unchanged, but the target is rotated through 180 degrees. In each case the desired effect is the same, namely to select first and second portions of the non-zero order diffracted radiation which are symmetrically opposite one another in the diffraction spectrum of the target.

While the optical system used for imaging in the present examples has a wide entrance pupil which is restricted by the field stop 21, in other embodiments or applications the entrance pupil size of the imaging system itself may be small enough to restrict to the desired order, and thus serve also as the field stop. Different aperture plates are shown in FIGS. 3(c) and (d) which can be used as described further below.

Typically, a target grating will be aligned with its grating lines running either north-south or east-west. That is to say, a grating will be aligned in the X direction or the Y direction of the substrate W. Note that aperture plate 13N or 13S can only be used to measure gratings oriented in one direction (X or Y depending on the set-up). For measurement of an orthogonal grating, rotation of the target through 90° and 270° might be implemented. More conveniently, however, illumination from east or west is provided in the illumination optics, using the aperture plate 13E or 13W, shown in FIG. 3(c). The aperture plates 13N to 13W can be separately formed and interchanged, or they may be a single aperture plate which can be rotated by 90, 180 or 270 degrees. As mentioned already, the off-axis apertures illustrated in FIG. 3(c) could be provided in field stop 21 instead of in illumination aperture plate 13. In that case, the illumination would be on axis.

FIG. 3(d) shows a third pair of aperture plates that can be used to combine the illumination modes of the first and second pairs. Aperture plate 13NW has apertures at north and east, while aperture plate 13SE has apertures at south and west. Provided that crosstalk between these different diffraction signals is not too great, measurements of both X and Y gratings can be performed without changing the illumination mode. A further variety of aperture plate 13Q will be illustrated in the example of FIGS. 12 and 13.

FIG. 4 depicts a composite grating target 700 (i.e. target comprising grating structures) formed on a substrate W according to known practice. The composite target 700 comprises four individual gratings 720 positioned closely together so that they will all be within a measurement spot 31 formed by the illumination beam of the metrology apparatus. The four gratings thus are all simultaneously illuminated and simultaneously imaged on sensors 19 and 23. In an example dedicated to overlay measurement, gratings 720 are themselves composite gratings formed by overlying gratings that are patterned in different layers of the semi-conductor device formed on substrate W. Gratings 720 may have differently biased overlay offsets in order to facilitate measurement of overlay between the layers in which the different parts of the composite gratings are formed. Gratings 720 may also differ in their orientation, as shown, so as to diffract incoming radiation in X and Y directions. In one example, gratings 32 and 34 are X-direction gratings with biases of +d, −d, respectively. This means that grating 32 has its overlying components arranged so that if they were both printed exactly at their nominal locations one of the components would be offset relative to the other by a distance d. Grating 34 has its components arranged so that, if perfectly printed, there would be an offset of d but in the opposite direction to the first grating and so on. Gratings 33 and 35 are Y-direction gratings with offsets +d and −d respectively. While four gratings are illustrated, another embodiment might require a larger matrix to obtain the desired accuracy. For example, a 3×3 array of nine composite gratings may have biases −4d, −3d, −2d, −d, 0, +d, +2d, +3d, +4d. Separate images of these gratings can be identified in the image captured by sensor 23.

FIG. 5 shows an example of an image that may be formed on and detected by the sensor 23, using the target 700 of FIG. 4 in the apparatus of FIG. 3, using the aperture plates 13NW or 13SE from FIG. 3(d). While the pupil plane image sensor 19 cannot resolve the different individual gratings 720, the image sensor 23 can do so. The cross-hatched rectangle 40 represents the field of the image on the sensor, within which the illuminated spot 31 on the substrate is imaged into a corresponding circular area 41. Ideally the field is dark. Within this dark field image, rectangular areas 42-45 represent the images of the individual gratings 720. If the gratings are located in product areas, product features may also be visible in the periphery of this image field. While only a single composite grating target is shown in the dark field image of FIG. 5, in practice a semiconductor device or other product made by lithography may have many layers, and overlay measurements are desired to be made between different pairs of layers. For each overlay measurement between pair of layers, one or more composite grating targets are required, and therefore other composite grating targets may be present, within the image field. Image processor and controller PU processes these images using pattern recognition to identify the separate images 42 to 45 of gratings 720.

Once the separate images of the gratings have been identified, the intensities of those individual images can be measured, e.g., by averaging or summing selected pixel intensity values within the identified areas. Intensities and/or other properties of the images can be compared with one another. These results can be combined to measure different parameters of the lithographic process. Overlay performance is an important example of such a parameter, and comparing the intensities reveals asymmetries that can be used as a measure of overlay. In another technique for measuring asymmetry and hence overlay, the pupil plane image sensor 19 is used.

Figure 6:
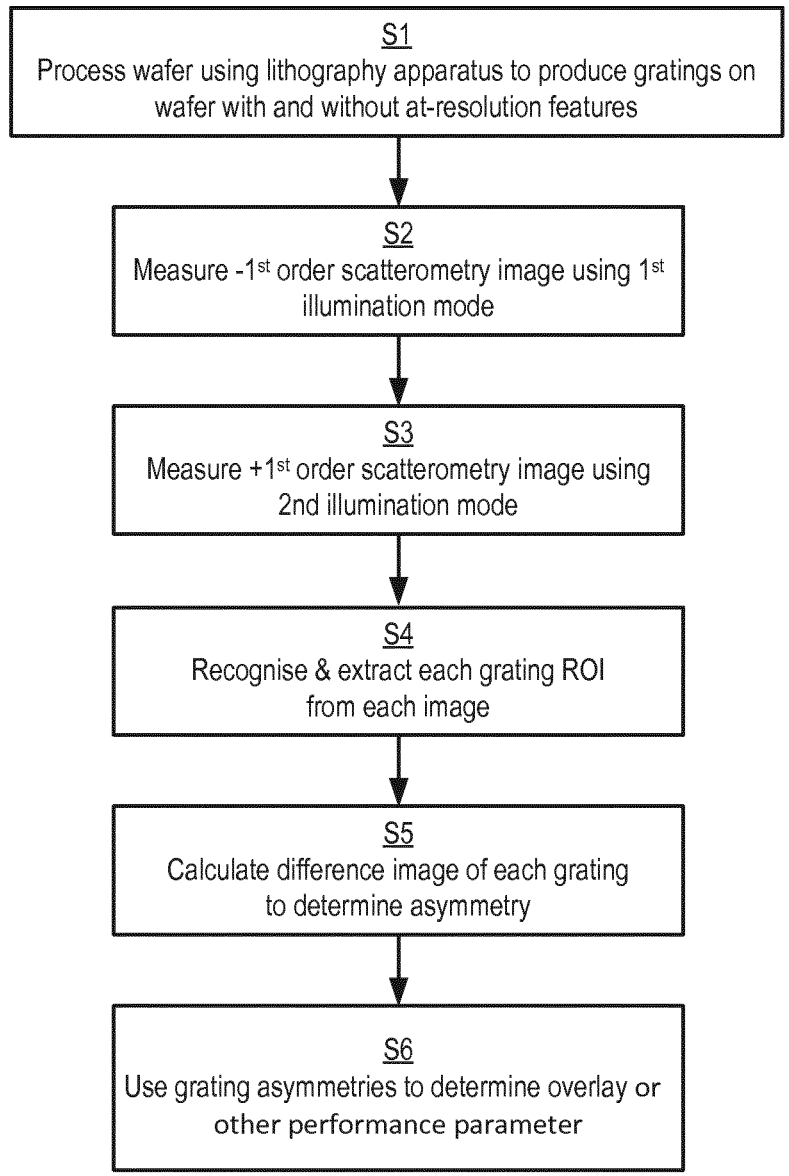
FIG. 6 is a flowchart showing the steps of a known overlay measurement method using the scatterometer of FIG. 3 and metrology target of FIG. 4, which can be adapted to implement embodiments of the present invention.

FIG. 6 illustrates a basic method of measuring overlay using the apparatus and targets described above. The invention is not limited to dark field techniques, nor even to angle-resolved scatterometry. The method in this example is based on the method described in application US 2011027704 using the apparatus of FIGS. 3 and 4. In principle, overlay error between the two layers containing the component gratings 720 is measured through asymmetry of the gratings, as revealed by comparing their intensities in the +1 order and −1 order dark field images. At step S1, the substrate, for example a semiconductor wafer, is processed through the lithographic cell of FIG. 2 one or more times, to create a structure including overlay gratings 720 that form a metrology target.

At S2, using the metrology apparatus of FIG. 3, an image of the gratings 720 is obtained using only one of the first order diffracted beams (say −1). Then, whether by changing the illumination mode, or changing the imaging mode, or by rotating substrate W by 180° in the field of view of the metrology apparatus, a second image of the gratings using the other first order diffracted beam (+1) can be obtained (step S3). Consequently the +1 diffracted radiation is captured in the second image. It is a matter of design choice whether all the gratings 720 can be captured in each image, or whether the scatterometer and substrate need to be moved so as to capture the gratings in separate images. In either case, it is assumed that first and second images of all the component gratings are captured via image sensor 23.

Note that, by including only half of the first order diffracted radiation in each image, the 'images' referred to here are not conventional dark field microscopy images. Each grating will be represented simply by an area of a certain intensity level. The individual grating lines will not be resolved, because only one of the +1 and −1 order diffracted radiation is present. In step S4, a region of interest (ROI, see FIG. 4) is carefully identified within the image of each component grating, from which intensity levels will be measured. This is done because, particularly around the edges of the individual grating images, intensity values can be highly dependent on process variables such as resist thickness, composition, line shape, as well as edge effects generally.

Having identified the ROI for each individual grating and measured its intensity, the asymmetry of the grating structure, and hence overlay error, can then be determined. As described in the prior applications, this is done by the image processor and controller PU in step S5 comparing the intensity values obtained for +1 and −1 orders for each grating 720 to identify any difference in their intensity. The intensity difference is calculated at step S5 to obtain a measurement of asymmetry for each grating. At step S6, from the asymmetry measurements and from knowledge of the overlay biases of the gratings, a processor calculates overlay error in the vicinity of the target T.

Current applications using embedded metrology targets, such as μDBO targets, (partially) disregard the optimization of the entire target layout with respect to optimum detectability by the metrology apparatus. For example, grating to grating distance, edge effect issues, and failure to maximize the available grating area, may lead to the following issues:
  1.—If large edge effects at each grating's periphery are observed in the dark field image:
    The size of available region of interest (ROI) may be reduced (due to cropping of the image to exclude the grating edges), leading to a poor reproducibility of the calculated signal.
    The accuracy of the calculated grating signal (average intensity) may be reduced due to contamination of the signal by optical crosstalk from emission due to edge effects.
    Instances of pattern recognition failure may be increased due to a varying image with pronounced edge-effects over the wafer and process variations in time.
    The sensitivity of the calculated signal to ROI-positioning errors may be increased; for example, should the large edge intensities be accidentally included into the signal estimation.
    The use of the full-scale (of the full dynamic gray-level range) of the CCD sensor may be reduced, leading to a reduced reproducibility and sensitivity to systematic non-linear camera issues at low gray levels.
  2.—The total area comprising grating structures is not maximized within the target region. Therefore, the maximum photon count is not reached (i.e. not optimized for reproducibility).

Figure 7:
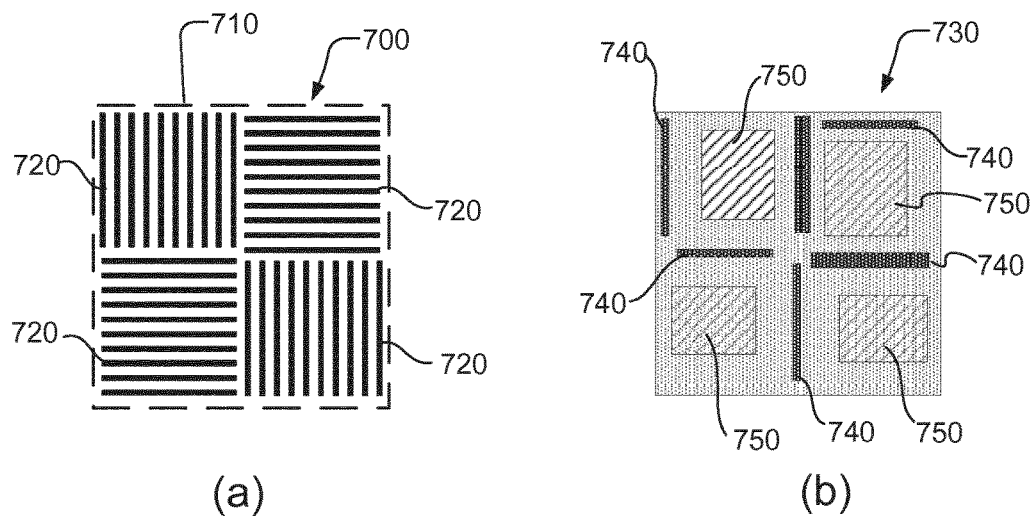
FIG. 7(a) depicts an example of non-optimized target layout; and (b) depicts the resulting dark field image.

FIG. 7(*a*) gives an example of a target 700 layout comprising four grating structures 720. Dashed shape 710 represents the available target area. As can be seen in FIG. 7(*a*), the target 700 layout is not optimized for the available target area 710. The number of grating lines is calculated as a function of pitches and the available target area 710. Subsequently, the predefined grating lines are centered at the predetermined grating midpoint. This results in non-optimized grating to grating distances (i.e. space between grating structures is not optimized within the target area). FIG. 7(*b*) illustrates a resultant dark field image 730 following inspection of the target 700. Regions of medium/high intensity levels 750 can be seen at the grating positions. However, at the grating periphery there are regions of even higher intensity levels 740 resultant from edge effects. This may make the target difficult to analyze using a pattern recognition process, leading to failure-prone pattern recognition.

The inspection tool used to measure the target 700 effectively acts as a frequency band filter. When the inspection tool measures a single grating 720, it actually detects two structure types. The first structure is that comprising the repeating grating lines, having a certain pitch. The second structure is the set of lines seen as a single entity having a certain size (half pitch); as these gratings are so small, they may be seen as single structures as well as gratings. Both of these "structures" give their own sets of Fourier frequencies. If these two sets do not fit together they will create a step Fourier frequency set. The last frequency set will always have one or more frequencies that will pass the band filter of the inspection tool. Unfortunately, the intensity of these frequencies is high thereby causing the edge effects. In many cases the edge effects result in intensities that are 2 to 4 times greater than the intensity of the maximum intensity grid.

To optimize target layout/designs for improved metrology tool detection, embodiments described herein propose to use:

1—Optimization of the target layout taking into account the full available target area.
2—. Computational lithography modeling using methods similar to optical proximity correction (OPC) to optimize the target layout for improved metrology process response (as opposed to only optimizing for the ability to print the target using a lithographic process). The resultant targets may use metrology tool-driven optical proximity correction (MT-OPC) assist features to aid in optimization of the metrology process response.

For example, optimization of a target layout may begin by placing MT-OPC assist features at the periphery of the available target area, so as to 'isolate' the target from the environment and to reduce the edge effects of the gratings in the dark field image. These assist features are not observed in the dark field image captured by the metrology apparatus, as their higher diffraction orders are usually not transmitted to the CCD sensor (noting that the zeroth order is also blocked).

Subsequent to this, the available target area, inside of the MT-OPC assist features, is filled with grating lines. For each grating this may be done in the direction towards the center, beginning from the periphery. Grating lines may be positioned in this way, while adapting their length to fit commensurately with the desired pitches and line space values of the neighboring grating. Additional MT-OPC assist features may be positioned between the gratings to reduce the grating edge effects and separate the gratings in the dark field image. Consequently each grating may have MT-OPC assist features around its whole periphery. Such target layouts help to improve pattern recognition and to limit crosstalk.

The optimization of a full target design may comprise 3 steps:

1—Optimization of the gratings with respect to design restrictions. Such design restrictions depend on the application given a specific product design, for example: line widths, sub segmentation, line on line or line on trench.
2—Optimization of the whole target layout for optimum metrology process detection, in some cases using MT-OPC assist features. Sub segmentation and/or other design restrictions may be applied to the MT-OPC assist features, where appropriate.
3—Performing lithography OPC cycles to the entire target layout to ensure that the desired target layout devised in steps 1 and 2 is properly printed on the wafer.

Figure 8:
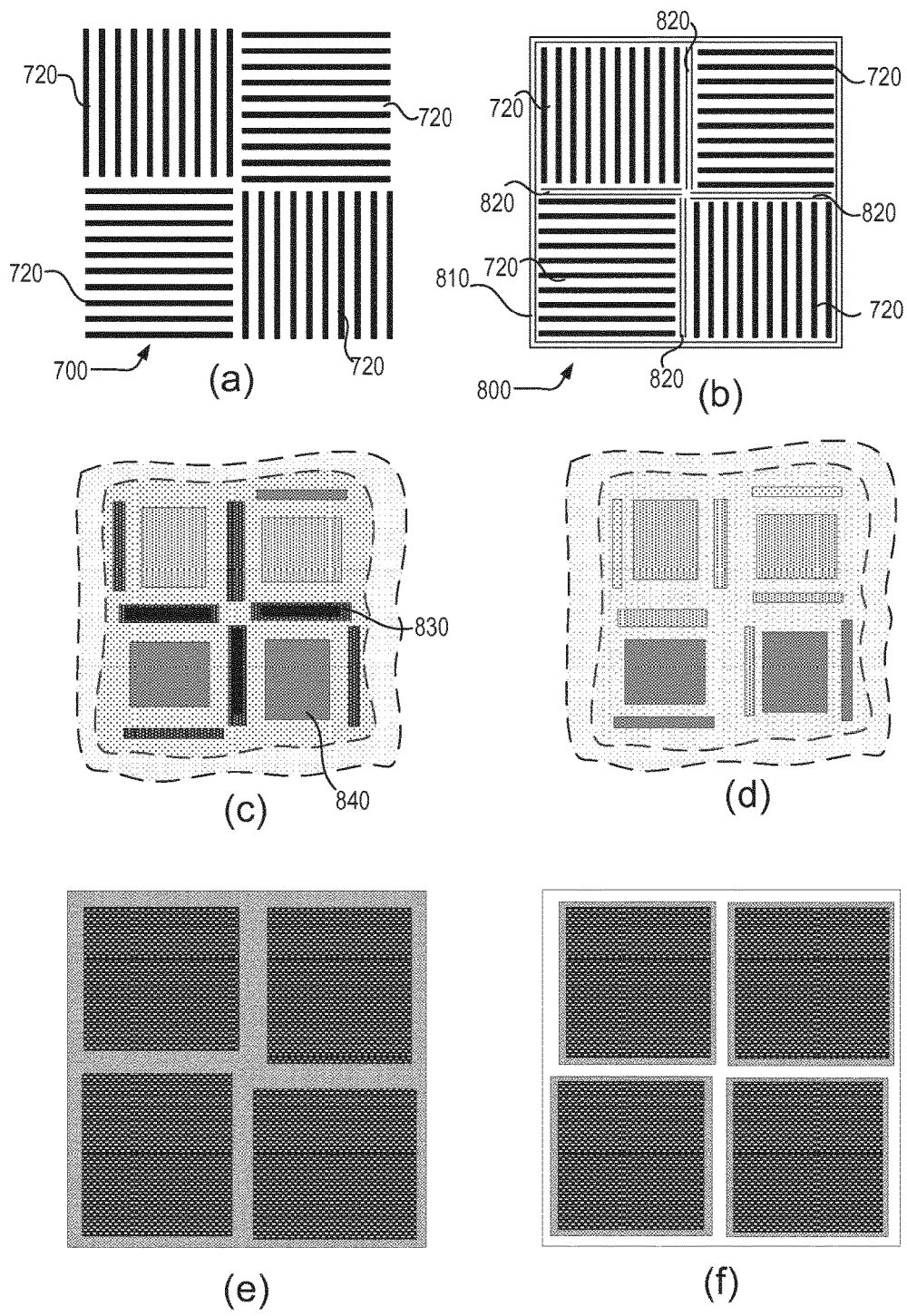
FIG. 8 (a)

FIG. 8 shows examples of a 10×10 µm² target design. FIG. 8(a) shows a non-optimized 600-nm pitch target layout 700 (similar to that shown in FIG. 7) comprising four grating structures 720. Each grating structures 720 comprises a plurality of grating substructures 760 (grating lines). FIG. 8(b) shows an improved version of the target layout 800 of FIG. 8(a), comprising identical grating structures 720 to that of the FIG. 8a arrangement, and further comprising MT-OPC assist features 810, 820. A first set of MT-OPC assist features 810 are located around the periphery of the target, so as to surround it, and a second set of MT-OPC assist features 820 are located between each grating. In this way, each grating 720 is surrounded by MT-OPC assist features 810, 820. FIG. 8(c) illustrates a dark field image simulation result of the target layout of FIG. 8(a), at 650 nm-wavelength. FIG. 8(d) illustrates a dark field image simulation result of the target layout of FIG. 8(b), using 650 nm-wavelength inspection radiation. FIG. 8(e) illustrates a dark field image simulation result of the of target layout FIG. 8(a), using 425 nm-wavelength inspection radiation. FIG. 8(f) illustrates a dark field image simulation result of the target layout of FIG. 8(b), using 425 nm-wavelength inspection radiation. In FIGS. 8(c) to 8(f), regions with darker shading indicate higher intensities.

A comparison of FIGS. 8(c) and 8(d) shows a far more uniform intensity distribution in the region of each grating, with fewer edge effects. These edge effects can be seen as regions of very high intensity measurements 830 at the periphery of the grating regions 840. A comparison of FIGS. 8(e) and 8(f) shows enhanced dark field image resolution, with improved separation of the gratings (i.e., lower intensity between gratings in FIG. 8(f) when compared to FIG. 8(e)), improving dark field pattern recognition.

Optimization of the target may include optimization of any parameter or aspect of the target. This can include inter alia grating pitch, MT-OPC assist feature pitch, length and width of any feature, grating duty cycle. The optimization process takes into account the entire available target region. In this example, the MT-OPC assist features have a smaller pitch (for example, of the order of 160 nm, resulting in evanescent waves). The MT-OPC assist features provide edge effect reduction and separation of the grating from the environment.

Figure 9:
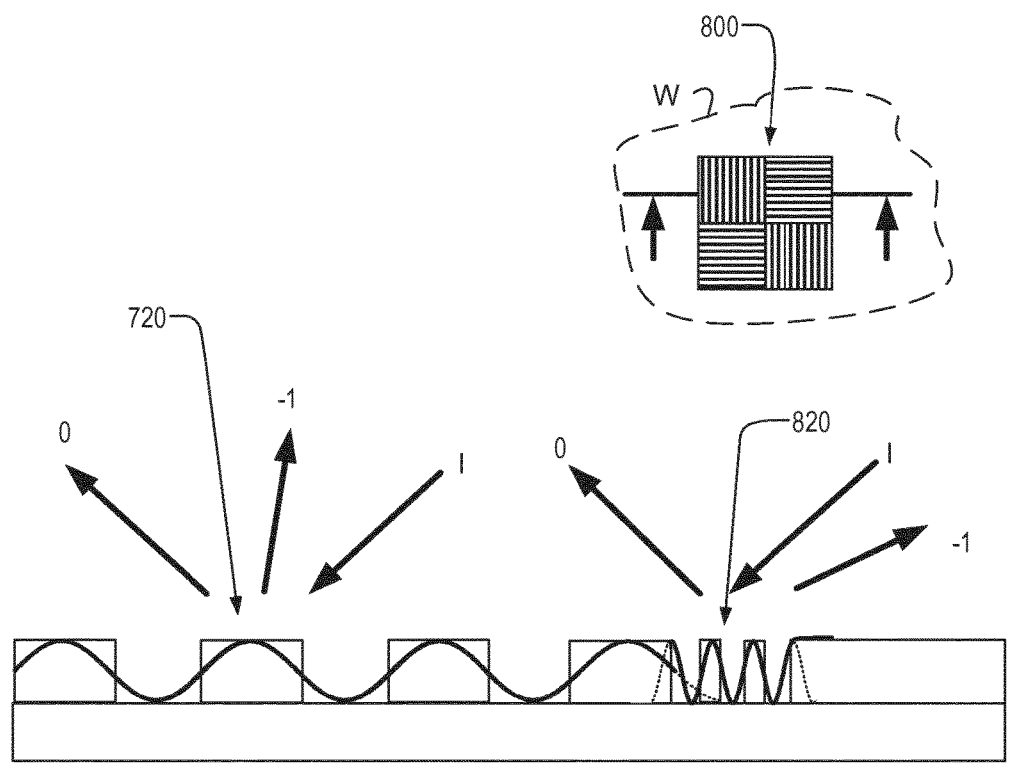
FIG. 9 illustrates a partial cross section of a target according to an embodiment of the invention.

FIG. 9 illustrates a magnified, partial view of a cross section of a target 800 comprising a grating 720 and MT-OPC assist features 820. The MT-OPC assist features 820 are positioned in the grating space-line-space rhythm, avoiding abrupt steps. In this way, the assist features 820 are positioned close to the grating 720 lines, while breaking the excitations within the grating resultant from its finite dimensions. Ensuring that the grating 720 and MT-OPC assist features 820 are in phase with each other avoids the "step frequency set" that causes high-intensity edge effects. The grating 720 and the MT-OPC assist features 820 being in phase means that the MT-OPC assist features 820 extend the continuous surface of the grating 720. While there still are edge effects, those of high intensity are outside of transmission band of the inspection tool and are not detected by it. In this way intensity peaks actually measured by the inspection tool are reduced.

Optical waves diffracted from these assist features 820 nominally do not carry any energy (evanescent or destructively interfering), or are outside the part of the spectrum that is transmitted to the detector (blocked propagating waves). In this specific example, Incident radiation I, diffracted zeroth order radiation 0 and first order radiation −1 is shown. The −1 order radiation diffracted by assist features 820 is blocked, and only −1 order radiation diffracted by grating 720 is transmitted to the sensor. However, due to the finiteness of the assist features 820, the 'tails' of the assist feature reflections will leak into the spectrum transmitted to the CCD sensor and will interact with the grating lines spectrum.

For well separated gratings in the dark field image it is recommended that the MT-OPC assist features 820 fill a space between the gratings having a width that is at least half the wavelength of the inspection tool. The same holds for the separation and crosstalk reduction from the environment on the target.

The potential target layout may be evaluated in a suitable metrology sensor simulation tool. It may require several iterations to arrive at an optimum target layout specific for the sensor configurations.

FIG. 10(a) shows a target arrangement, where a target 1000 occupies, in practice, an area of 12×12 μm² 1010. The target layout includes a 1 μm 'clearance' region 1020 at the target boundaries, to improve dark field pattern recognition and reduce crosstalk from the environment. In FIG. 10(b), the target layout of FIG. 10(a) is replaced by a target layout 1030 optimized for the entire target region of 12×12 μm². The target layout includes MT-OPC assist features 1035 around its periphery, and further MT-OPC assist features 1040 between each grating 1050. The MT-OPC assist features 1035, 1040 guarantee the dark field pattern recognition performance and the optical crosstalk reduction from the environment, such that the 'clearance' region 1020 will not be needed. Therefore, the size, number of lines and pitch of each grating 1050 can be optimized to the available target area 1010. The corresponding dark field image simulation results (not illustrated) show that the edge effects are strongly reduced, while pattern recognition is improved by the grating to grating separation.

Figure 11:
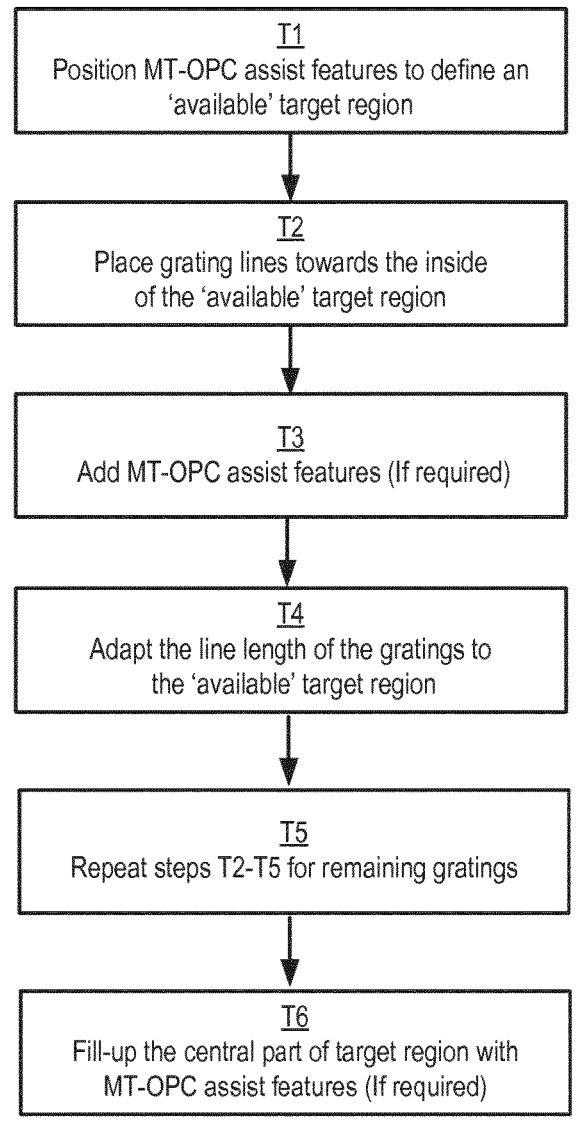
FIG. 11 is a flowchart of a method of devising a target arrangement according to an embodiment of the invention.

FIG. 11 is a flowchart illustrating a method of devising a target arrangement. The method comprises the following steps:

Step T1—Draw MT-OPC assist features, with 'sub-resolution' pitches, for example, near the boundaries and/or inside a target region. This defines an 'available/empty' target region. The characteristics of the assist features (e.g. line width, shape . . . ) may be chosen, for example, to efficiently isolate the target from the environment in the dark field image.

Step T2—Based on the MT-OPC assist features placed at the target boundaries, place the grating lines of the first grating sequentially in a direction towards the inside of the target region, beginning at the boundary. Place lines for example, until part of the last placed line is located over a halfway point of the available target area in the grating direction.

Step T3—Add MT-OPC assist features (if needed), having a form based on the size and pitch of the grating lines, and further having 'sub-resolution' pitches.

Step T4—Based on the latter MT-OPC assist features, adapt the line length of the next grating to the remaining available target region.

Step T5—Repeat steps T2-T4 for the remaining gratings.

Step T6—Optionally, fill-up the central part of target region with MT-OPC assist features.

Figure 12:
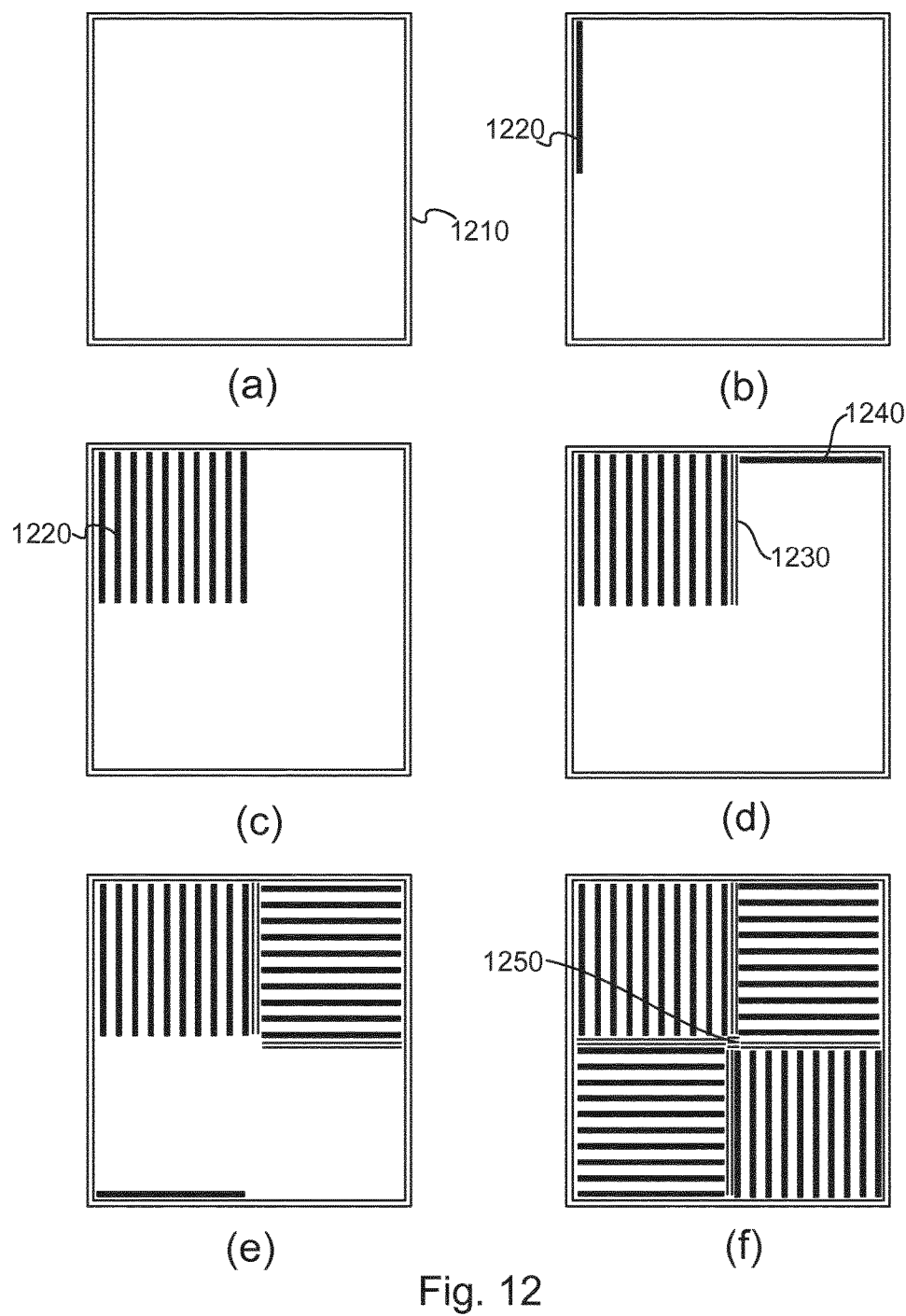
FIG. 12(a), FIG. 12(b), FIG. 12(c), FIG. 12(d), FIG. 12(e) and FIG. 12(f) illustrate the method depicted in FIG. 11 being performed to devise a target arrangement.

An example application of this method is illustrated in FIG. 12. FIG. 12(a) corresponds to step T1. MT-OPC assist features 1210 are drawn close to the border of available target region, with a pitch chosen to isolate the target from the environment and to reduce grating edge effects. FIGS. 12(b) and (c) correspond to step T2, with grating lines 1220 placed so as to fill up approximately one quarter of the target region allocated to this grating structure. FIG. 12(d) corresponds to step T3, with further MT-OPC assist features 1230 added, matched to the grating lines. FIG. 12(d) also illustrates the beginning of step T4, with the line length of line 1240 having been adapted to the remaining available area. FIG. 12(e) corresponds to an intermediate point during step T5, with two gratings placed and a third begun. FIG. 12(f) illustrates the completed target arrangement, with additional MT-OPC assist features 1250 placed within a central region of the target layout as described in step T6. This method may require several iterations, with each target arrangement obtained at step T6 being evaluated using metrology simulation tools. Evaluation may comprise determining whether a particular arrangement meets one or more predefined criteria and/or comparing multiple different arrangements devised in accordance with this method so as to determine the best one (based on one or more predefined criteria).

Instead of filling the central region of the target with additional MT-OPC assist features 1250, this region could be filled with special target (cross) for performing reticle writing quality measurements.

This method may be carried out, preferably, in an automated fashion. An 'automated' method includes (not exclusively) (i) accurate optical models that can predict accurately the metrology apparatus response, within an acceptable timeframe and (ii) well defined criteria for optimization. For example, optimization criteria may include:

Grating edge intensities having the same order of magnitude as the grating center intensities.

Minimum variation of edge effects in the presence of overlay, defocus and aberrations of the metrology sensor.

Sufficient spacing between the grating structures for optimum target pattern recognition, for the relevant wavelength range (spacing $\geq \lambda/2$, with $\lambda$ representing the inspection wavelength).

Maximum grating area.

Ideally these criteria are balanced in devising the final target arrangement.

Overlay metrology requires two stacked gratings (i.e. a two layer target). For such targets, the bottom target layout may be devised using the method of FIG. 12. The top grating structures usually contain the overlay biases, ranging from five to several tens of nanometers. In such an arrangement, the top target arrangement may simply match the bottom grating structures, with the exception of the bias(es). In an example, the bias may be applied to only the grating lines in the top target layer, with no bias applied to the MT-OPC assist features in this top layer. Alternatively, MT-OPC assist features can be omitted in the top layer. This latter approach may help avoid generation of an asymmetric signal perturbing the overlay measurement, and is especially applicable if the back-reflected diffraction of the top grating structures is weak and the main back-reflected diffraction originates from the bottom grating structures.

For line-on-trench instead of line-on-line target configurations, the top grating layout may be inverted, to obtain the line-on-trench configuration. For duty-cycles which differ from 50%, it is possible to design the top target as the line-on-line version with a reverse duty cycle (100% —duty-cycle), which is then inverted to obtain the line-on-trench configuration. The design of MT-OPC assist features in case of duty-cycle differences between top and bottom grating structures may lead to a more complex layout optimization procedure, however, those skilled in the art will be able to implement and customize the present method for such arrangements.

Note that to guarantee printability and compliance with semiconductor manufacturer design rules, dimensions of MT-OPC assist features may allow sub-segmentation of these MT-OPC assist features.

The dimensions and/or shape of MT-OPC assist features may be customized to the needs of the application. For instance, in the example of FIG. 9, MT-OPC assist features 820 are represented by 'continuous square' shapes. However, continuous square shapes may lead to electric charging effects on the reticles or printed circuits at sharp edges. To overcome this issue, shapes edges may be 'deleted' from the layout.

In the above mentioned examples, the MT-OPC assist features are 'sub-resolution' (i.e., have a smaller resolution than that of the product features). However, the MT-OPC assist features may have dimensions below, within or above the resolution of the sensor, depending on the application.

The present method for optimizing target layout/design may be applied, for example, during design/optimization processes of metrology/alignment targets for all metrology applications (including alignment). For example, the present method may be applied to alignment targets used in overlay correction systems and/or in advanced alignment systems.

As shown in the above examples, MT-OPC assist features may be placed at the target boundaries and/or may be placed around each grating structure in order reduce edge effects. In addition to this, MT-OPC assist-features may be placed between the grating structure lines (e.g. for a large pitch grating structure such as an alignment grating) in order to sharpen or soften line trench transitions. This may help enhancement of the diffraction efficiency into desirable orders by optimizing the intrinsic diffraction efficiency for the detected orders, or optimizing the ordering of energy into the relevant diffraction orders. This may aid detectability for low 'wafer quality' stacks. Furthermore, the gain set point in the alignment sensor electronics may be improved, particularly for low wafer quality stacks, during the read-out and scanning over the alignment target.

The present method may also be combined with current methods for improving parameter estimation in, for example, dark field metrology.

The methods disclosed above result in larger ROIs and consequently, larger photon counts during intensity measurements. This improves the reproducibility for a constant target region. Improved reproducibility may also be resultant from the reduction of edge effects, reducing inaccuracy in ROIs positioning. In addition, reduction of edge effects improves pattern recognition as a consequence of a better defined dark field target image. Furthermore, the full gray scale dynamic range of the camera may be used as edge effects will not saturate the dark field image. Consequently, reproducibility is further improved and non-linear camera effects which result from photon noise at low intensities are avoided. Photo noise is the square root of the number of measured photons. The number of measured photons is the product of the number of used pixels, the gray level and the sensitivity. To obtain a more stable measurement either the number of pixels or number of gray levels needs to be increased; camera sensitivity is fixed. By using the MT-OPC assist features more gray levels can be obtained.

Adding MT-OPC assist features to individual grating structures improves the isolation from the in-die environment when distributing each grating structure separately among device structures. The flexibility for in-die placement of the targets/gratings is therefore improved due to the isolation of the gratings from the surroundings.

Finally, the target region may also be reduced (i.e. smaller target dimensions) while keeping a same reproducibility. Reduced target dimensions enable denser intra-field measurements. This improves higher order overlay corrections over the die on on-product wafers and scanner performance characterization.

While the target structures described above are metrology targets specifically designed and formed for the purposes of measurement, in other embodiments, properties may be measured on targets which are functional parts of devices formed on the substrate. Many devices have regular, grating-like structures. The terms 'target grating' and 'target structure' as used herein do not require that the structure has been provided specifically for the measurement being performed. The term "structure" is used herein without limitation to any particular form of structure such as a simple grating line. Indeed, coarse structural features, such as the lines and spaces of a grating, can be formed by collections of finer sub-structures.

In association with the physical grating structures of the targets as realized on substrates and patterning devices, an embodiment may include a computer program containing one or more sequences of machine-readable instructions describing a methods of producing targets on a substrate, measuring targets on a substrate and/or analyzing measurements to obtain information about a lithographic process. This computer program may be executed for example within unit PU in the apparatus of FIG. 3 and/or the control unit LACU of FIG. 2. There may also be provided a data storage medium (e.g., semiconductor memory, magnetic or optical disk) having such a computer program stored therein. Where an existing metrology apparatus, for example of the type shown in FIG. 3, is already in production and/or in use, the invention can be implemented by the provision of updated computer program products for causing a processor to perform the modified steps S4-S6 and so calculate, for example, overlay error to be corrected. The program may optionally be arranged to control the optical system, substrate support and the like to perform automatically the steps S2-S5, etc. for measurement of asymmetry on a suitable plurality of target structures.

In an embodiment, there is provided a method of devising a target arrangement, the target comprising a plurality of gratings, each grating comprising a plurality of substructures, the method comprising: defining a target area; locating the substructures within the target area so as to form the gratings; and locating assist features at the periphery of the gratings, the assist features being configured to reduce measured intensity peaks at the periphery of the gratings.

In an embodiment, the locating the substructures comprises forming each individual grating sequentially. In an embodiment, the locating the substructures comprises, for each grating, locating the substructures sequentially beginning from the target area periphery towards the target area center. In an embodiment, the method comprise, before locating the substructures forming a particular grating, adapting the length of the grating substructures to the remaining target area. In an embodiment, the assist features which are adjacent to and orientated with a particular grating are positioned in phase with that grating. In an embodiment, the assist features comprise first assist features and the target area is defined by a plurality of the first assist features substantially surrounding the target area. In an embodiment, the assist features comprise second assist features which are provided between each grating within the target area. In an embodiment, the second assist features are located to fill a space between the gratings comprising at least a half a wavelength of the relevant inspection wavelength. In an embodiment, each grating is substantially surrounded by the assist features so as to isolate each grating from its surrounding environment. In an embodiment, the assist features comprise lines having a pitch substantially smaller than the grating pitch. In an embodiment, the pitch of the assist features is such that the assist features are not detected during inspection of the target using a metrology process. In an embodiment, assist features are located immediately adjacent each outermost substructure of each grating. In an embodiment, each grating has approximately equal area. In an embodiment, the method comprises modelling a resultant image obtained by inspection of the target using a metrology process and evaluating whether the target arrangement is optimized for detection using a metrology process. In an embodiment, the method is repeated iteratively in order to optimize the target arrangement. In an embodiment, the criteria for considering whether a particular target arrangement is considered optimized include one or more of: determining whether intensities at grating periphery are of the same order of magnitude as those at the grating center, when inspected using the diffraction based metrology process; determining whether there is minimum intensity variation at the grating periphery in the presence of overlay, defocus and aberrations when inspected using the diffraction based metrology process; determining whether there is sufficient spacing between the gratings for optimum target-recognition for the relevant inspection wavelength range; and determining whether the total grating area is maximized. In an embodiment, the target comprises two or more overlaid target layers, with the top target layer comprising an overlay bias, and wherein the bias is not applied to assist features comprised in the top layer. In an embodiment, the target comprises two or more overlaid target layers, with the top target layer comprising an overlay bias, and wherein the top layer does not comprise any assist features.

In an embodiment, there is provided a target comprising: a plurality of gratings, each grating comprising a plurality of substructures; assist features comprising lines having a pitch substantially smaller than the pitch of the gratings; wherein the target comprises assist features at the periphery of the gratings, the assist features being configured to reduce measured intensity peaks at the periphery of the gratings.

In an embodiment, each grating is substantially surrounded by the assist features so as to isolate each grating from its surrounding environment. In an embodiment, the assist features comprise first assist features and the target area is defined by a plurality of the first assist features substantially surrounding the target area. In an embodiment, the assist features comprise second assist features which are provided between each grating within the target area. In an embodiment, the assist features comprise lines having a pitch substantially smaller than the grating pitch. In an embodiment, the pitch of the assist features is such that the assist features are not detected during inspection of the target using a metrology process. In an embodiment, the assist features are configured to reduce diffraction intensity peaks at each grating periphery. In an embodiment, assist features are located immediately adjacent each outermost substructure of each grating. In an embodiment, the assist features which are adjacent to and orientated with a particular grating are in phase with that grating. In an embodiment, each grating has approximately equal area.

In an embodiment, there is provided a reticle comprising features' configured to form the target as described herein.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A method of devising a target arrangement, the target comprising a plurality of gratings, each grating comprising a plurality of substructures, the method comprising:
   defining a target area;
   locating the substructures within the target area so as to form the gratings;
   locating assist features at the periphery of the gratings, the assist features being configured to reduce measured intensity peaks at the periphery of the gratings; and
   before locating the substructures forming a particular grating, adapting the length of the grating substructures for that particular grating to a remaining target area such that the length of the substructures forming that particular grating is different than that of the substructures of another grating in the target area.

2. A method as claimed in claim 1, wherein the locating the substructures comprises forming each individual grating sequentially.

3. A method as claimed in claim 1, wherein the locating the substructures comprises, for each grating, locating the substructures sequentially beginning from the target area periphery towards the target area center.

4. A method as claimed in claim 1, wherein the assist features which are adjacent to and orientated with a particular grating are positioned in phase with that grating.

5. A method as claimed in claim 1, wherein each grating is substantially surrounded by the assist features so as to isolate each grating from its surrounding environment.

6. A method as claimed in claim 1, wherein a pitch of the assist features is such that the assist features are not detected during inspection of the target using a metrology process.

7. A method as claimed in claim 1, wherein assist features are located immediately adjacent each outermost substructure of each grating.

8. A method as claimed in claim 1, wherein each grating has approximately equal area.

9. A method as claimed in claim 1, wherein the target comprises two or more overlaid target layers, with the top target layer comprising an overlay bias, and wherein the bias is not applied to assist features comprised in the top layer.

10. A method as claimed in claim 1, wherein the target comprises two or more overlaid target layers, with the top target layer comprising an overlay bias, and wherein the top layer does not comprise any assist features.

11. A method as claimed in claim 1, comprising modelling a resultant image obtained by inspection of the target using a metrology process, and evaluating whether the target arrangement is optimized for detection using a metrology process.

12. A method as claimed in claim 11, wherein the method is repeated iteratively in order to optimize the target arrangement.

13. A method as claimed in claim 11, wherein criteria for considering whether a particular target arrangement is considered optimized include one or more selected from:
  determining whether intensities at a grating periphery are of the same order of magnitude as those at a grating center, when inspected using a diffraction based metrology process;
  determining whether there is minimum intensity variation at a grating periphery in the presence of overlay, defocus and/or aberrations when inspected using a diffraction based metrology process;
  determining whether there is sufficient spacing between the gratings for optimum target-recognition for a relevant inspection wavelength range; and/or
  determining whether a total grating area is maximized.

14. A target comprising:
  a plurality of gratings, each grating comprising a plurality of substructures;
  assist features comprising lines having a pitch substantially smaller than the pitch of the gratings and separated from the substructures,
  wherein the target comprises assist features at the periphery of the gratings, the assist features configured to reduce measured intensity peaks at the periphery of the gratings, and
  wherein the assist features which are adjacent to and orientated with a particular grating are positioned in phase with the substructures of that grating.

15. A reticle comprising features configured to form the target as claimed in claim 14.

16. A target as claimed in claim 14, wherein a length of the substructures for one of the plurality of gratings is different than that of the substructures of another grating of the plurality of gratings.

17. A target as claimed in claim 16, wherein each grating has approximately equal area.

18. A method of devising a target arrangement, the target comprising a plurality of gratings, each grating comprising a plurality of substructures, the method comprising:
  defining a target area;
  locating the substructures within the target area so as to form the gratings;
  locating assist features within the target area, the assist features configured to reduce measured intensity peaks at the periphery of the gratings;
  modelling a resultant image obtained by inspection of the target using a metrology process; and
  evaluating whether the target arrangement is optimized for detection using a metrology process,
  wherein criteria for considering whether a particular target arrangement is considered optimized include one or more selected from:
    determining whether intensities at a grating peripheral portion are of the same order of magnitude as those at a grating central portion, when inspected using a diffraction based metrology process,
    determining whether there is minimum intensity variation at a grating peripheral portion in the presence of overlay, defocus and/or aberrations when inspected using a diffraction based metrology process,
    determining whether there is sufficient spacing between the gratings for optimum target-recognition for a relevant inspection wavelength range, and/or
    determining whether a total grating area is maximized.

19. A method as claimed in claim 18, wherein the assist features which are adjacent to and orientated with a particular grating are positioned in phase with that grating.

20. A method as claimed in claim 18, further comprising adapting the length of the grating substructures for, or an overall length of, a particular grating to a remaining target area such that that length of the grating substructures or overall length is different than that of another grating in the target area.

* * * * *